United States Patent [19]

Bagley et al.

[11] 4,329,526

[45] May 11, 1982

[54] CHLORINATION METHOD

[75] Inventors: Melvin R. Bagley; Burton B. Crocker; John F. Pysz, all of St. Louis, Mo.

[73] Assignee: Monsanto Company, St. Louis, Mo.

[21] Appl. No.: 207,514

[22] Filed: Nov. 17, 1980

Related U.S. Application Data

[63] Continuation-in-part of Ser. No. 106,798, Dec. 26, 1979, abandoned.

[51] Int. Cl.³ .................... C07C 17/15; F26B 17/00
[52] U.S. Cl. ............................. 570/203; 34/57 A; 422/143; 422/139; 570/243
[58] Field of Search ............... 422/143, 139; 570/203, 570/243

[56] References Cited

U.S. PATENT DOCUMENTS

| | | | |
|---|---|---|---|
| 2,798,030 | 7/1957 | Hettick et al. | 196/52 |
| 2,910,431 | 10/1959 | Sage et al. | 422/143 |
| 2,957,757 | 10/1960 | Coates et al. | 23/284 |
| 3,345,422 | 10/1967 | Piester et al. | 260/654 A |
| 3,818,606 | 6/1974 | Marcellini | 34/57 A |
| 3,863,359 | 2/1975 | Grega | 34/57 R |

*Primary Examiner*—Arthur P. Demers
*Attorney, Agent, or Firm*—Thomas Y. Awalt, Jr.

[57] ABSTRACT

An improvement in fluid-bed oxychlorination methods comprising in combination a generally cup-shaped container and an inverted generally cone-shaped gas distributor having a truncated apex the section of truncation defining a generally circular or polygonal opening, the lip portion of the container fitting against the similarly-shaped opening of the distributor.

8 Claims, 5 Drawing Figures

CHLORINATION METHOD

CROSS REFERENCE TO RELATED APPLICATION

This is a continuation-in-part of my co-pending application Ser. No. 106,798 filed Dec. 26, 1979, now abandoned.

BACKGROUND OF THE INVENTION

1. Field of the Invention

The invention relates to improvements in oxychlorination methods employing fluidized bed reactors in which fine particles of a material to be processed or to be made to react are held in suspension by an ascending stream of gas.

2. Description of the Prior Art

It is known in the art to prepare chlorinated hydrocarbons from saturated aliphatic hydrocarbons, their incompletely chlorinated derivatives and benzene by modified Deacon type chlorination procedures. An oxychlorination procedure of this type may conveniently involve the chlorination of the hydrocarbon and/or a chlorohydrocarbon with hydrogen chloride, an oxygen-containing gas such as air, or elemental oxygen in the presence of a metal halide catalyst at elevated temperatures. In a process of this nature the hydrogen chloride is believed to be oxidized in the presence of the catalyst to chlorine and water, and the chlorine liberated in this manner from the hydrogen chloride reacts with hydrocarbon or chlorinated hydrocarbon present in the feed gas to the reaction zone to form further chlorinated hydrocarbons and HCl. HCl produced by the chlorination part of this procedure has been further utilized by addition of oxygen in the process.

In a variation of an oxychlorination process, elemental chlorine is used as the feed source. In this modernized operation, hydrogen chloride is generated by the chlorination of the hydrocarbon and/or hydrocarbon chloride fed with the elemental chlorine to the catalytic reaction zone. Thus, free chlorine, an oxygen containing gas, such as air, or oxygen itself, and a hydrocarbon and/or chlorohydrocarbon are passed in contact with a metal halide catalyst maintained at elevated temperatures. The chlorine presumably reacts with the hydrocarbon and/or chlorohydrocarbon to produce hydrogen chloride and a chlorinated derivative of the organic feed. The chlorine content of the hydrogen chloride produced in this manner is then utilized to achieve additional chlorinations by the standard Deacon-type reaction in which the hydrogen chloride is oxidized to water and elemental chlorine.

The present invention is concerned with operations of the above character which take place in fluidized beds. In discussing fluidized beds in the specification and claims, it is to be understood that the term "fluidized bed" is employed in the broad sense. In conducting fluid bed processes, gaseous reactants of varying velocities are passed upwardly through a bed of finely divided, solid catalyst containing particles. Such reactions are taught in U.S. Pat. No. 3,345,422, hereby incorporated by reference.

A common means for distribution of fluidizing gas in a reactor comprises a plate located at the base of the reactor through which an ascending current of fluidizing gas passes, and on which base the particles rest when the reactor is shut down. Alternatively, state-of-the-art reactors may have a dished or flat bottom with rows of pipe grids in a horizontal plane spaced some distance above the bottom for distribution of the fluidizing gas. The pipes may be arranged in many configurations such as parallel rows, concentric rings, or an outer ring with radial spokes resembling a wagon wheel. Holes are drilled in the pipes in a regular pattern for distribution of the gas within the bed; such holes may be oriented upward, downward, or horizontal.

The distributing plate, also called a grid, divides the reactor into two chambers namely; a first upper chamber constituting the treatment chamber into which the material in particulate form to be treated or to be made to react is introduced, and a second lower chamber called a "wind box" which is connected to the source of a gaseous fluidizing agent. In some of these reactors the grid is in the form of a plate of varying thickness usually of a refractory material, perforated with a multitude of holes of relatively small section through which the ascending stream of fluidizing gas passes. In some reactors, such multitude of holes are replaced by a much smaller number of cavities of much greater section, cutting through the grid and placing the wind box in communication with the treatment chamber. Dual perforated plates may be spaced close together with the holes staggered so as to prevent direct "line-of-sight" connection between the two chambers. Alternatively, the holes in the plate or plates may be equipped with caps, bubble caps, risers and tuyers or distributors, ball-check valves; or the plate may be made of sintered porous plates. In other reactors, the cavities are joined to a common source of fluidizing agent by means of gas supply ducts independent of one another.

Usually, the cross-sections of the holes or of the cavities are greater than the size of the particles constituting the material to be processed or to be reacted. When the speed of the ascending stream of fluidizing gas is inadequate or nonexistant, the particles which are not in a state of fluidized flow downwardly into or through the holes or the cavities and accumulate either in the wind box or in the ducts supplying fluidizing agent to the cavities. This may lead to the clogging of the ducts, which may necessitate either the cleaning of the ducts, or their replacement. Sometimes the presence of the solids in the fluidizing gas stream outside of the treatment chamber can result in undesired chemical reactions or decomposition resulting in poor yields, undesired by-products and impurities, or even hazardous or unsafe operating conditions.

To prevent this undesirable flow, reactor grids fitted with a wind box have been provided with fixed or stationary, even retractable valves, arranged either over or below the holes or the cavities, and intended to seal the said holes or the cavities at the proper times. These valves are not easily fitted to grids whose cavities are supplied with fluidizing gas independently of each other. The utilization of dual staggered-hole plate grids, hole caps, risers and tuyers and pipe grids with downwardly directed holes are all attempts to prevent such back flow of solids but which are only partially effective because semi-aerated solid particles negotiate the obstructions in these devices at the time of fluidizing gas shut-off, ball-check valves act as small grinding mills and reduce the particle size of the solid particles resulting in their loss through recovery equipment and resulting atmospheric pollution or downstream equipment plugging sintered porous plates prevent solids from weeping but are subject to pluggage by particulates in the fluidizing gas, and are difficult to install, seal, and replace.

In some fluid-bed processes, solids which are not fluidized or kept suspended are subject to hot spots, caking or production of off-grade products. Many distributors are incapable of placing all solids in suspension. Solids resting on plate distributors between cavities, or between hole caps, risers and tuyers, or below pipe distributors may be largely stagnant.

An object of the present invention is to improve state-of-the-art oxychlorination methods by avoiding the above-mentioned disadvantages. This is achieved by eliminating passages which can be blocked, or plugged while preventing weepage of the solids back to the windbox, eliminating stagnant, non-fluidized solids areas, and reducing solids attrition to that caused by gas-solids interaction.

Another object is to reduce distributor assembly corrosion and catalyst bridging problems in state-of-the-art oxychlorination methods.

SUMMARY OF THE INVENTION

The improvement in oxychlorination methods is through the use of an improved apparatus for the distribution of gas in a fluidized bed reactor. Pressurized gas is fed into a generally cup-shaped container directed toward the base of the container. The cup-shaped container opens upwardly into a truncated inverted generally cone-shaped gas distributor, the section of truncation defining an opening into which the cup-shaped container empties the fluidizing particles when pressurized gas is introduced therein.

BRIEF DESCRIPTION OF THE DRAWINGS

In the specification, reference will be made to the drawings in which.

DESCRIPTION OF THE PREFERRED EMBODIMENTS

Figure 1:
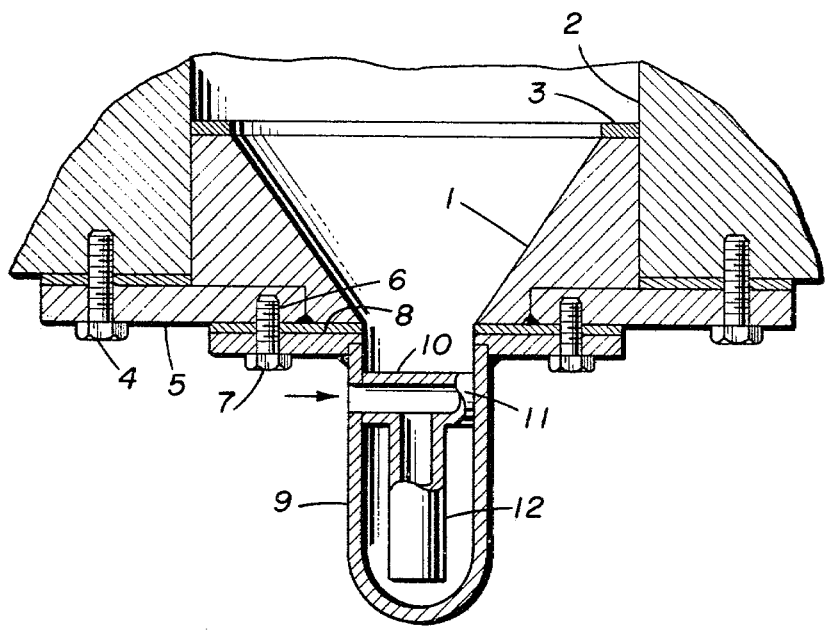
FIG. 1 is an elevation seen in cross-section of the base of a reactor.

Referring now in detail to all FIGURES, gas distributor cone 1 fits snuggly within the cylindrical walls of reactor 2, and against split ring seal 3. It is held in position at the bottom of the reactor by attaching bolts 4 through base plate 5. Threaded channel 6 receives cup-plate bolt 7 which, through cup plate 8, affixes the lip portion of cup 9 to the section defined by the truncation of inverted cone-shaped distributor 1. Pressurized gas is introduced into one side of T-shaped tube-like gas conduit 10 which is comprised of a horizontal cross-tube 11 and substantially vertical discharge tube 12, directed generally towards the base portion of the cup.

Figure 2:
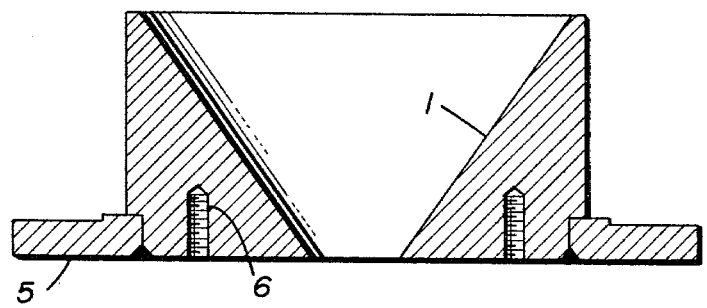
FIG. 2 is a cross-section shown along 2—2 of FIG. 3 depicting a truncated cone distributor.
Figure 3:
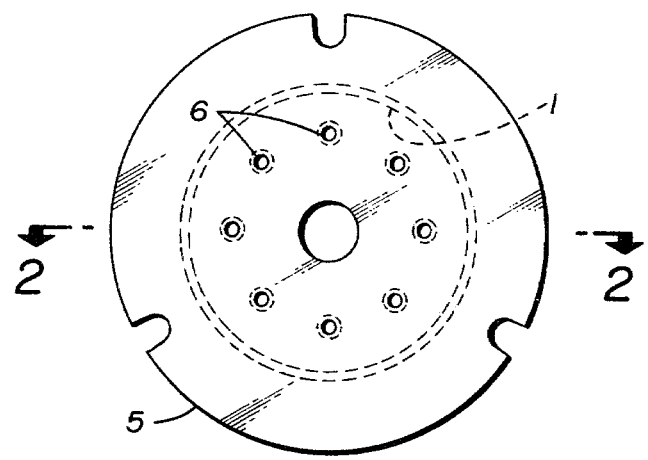
FIG. 3 is a top view of the distributor of FIGS. 1 and 2.

FIGS. 2 and 3 show in more detail cone-shaped gas distributor 1.

Figure 4:
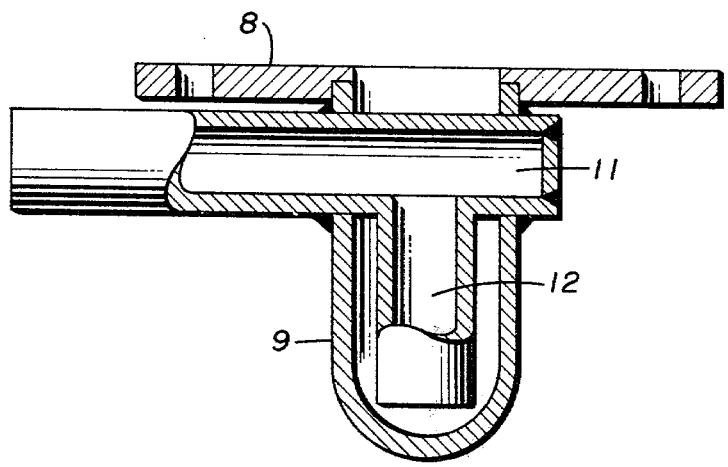
FIG. 4 is an elevation in section of a first preferred embodiment of the gas-introduction means into the generally cup-shaped container.

FIG. 4 shows in more detail cup-shaped container 1 and the T-shaped tube-like gas conduit 10 as described above.

Figure 5:
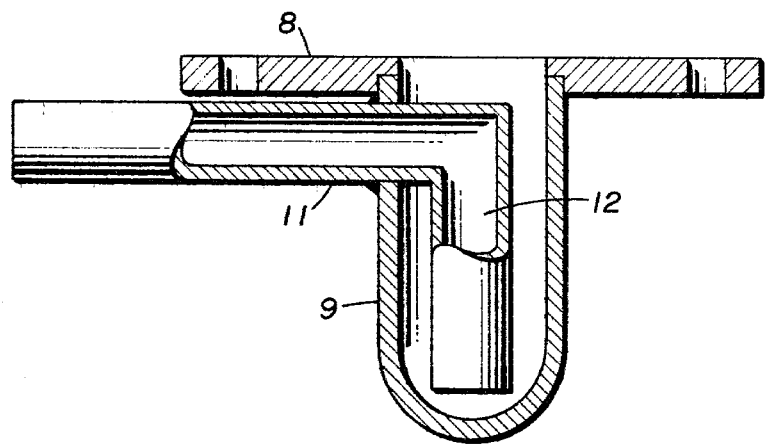
FIG. 5 is a second preferred embodiment of the gas-introduction means into the cup-shaped container.

FIG. 5 shows in more detail a second preferred embodiment wherein, instead of T-shaped tube-like gas conduit 10, an L-shaped tube-like gas conduit is substituted.

Cup 9 is described as "generally cup shaped" and distributor 1 as "generally cone shaped". While the figures show a cylindrical cup and conical gas distributor, it will be readily apparent to one skilled in the art, that a cup with polygon cross-section mated with a diverging cone of similar cross-section such as an octagon or a hexagon will work equally well. Even a cup of square cross-section can be used, provided the corners of the square are well rounded. These and other readily apparent variations are included in the term "generally" as applied to the cup and distributor. While the figures also show the conical distributor extending to the walls of a single treatment chamber, it will also be apparent that a multiplicity of distribution systems in parallel may be used to interconnect a single large windbox with a single large diameter fluidized treatment chamber. In such a case, distributors as shown can be bolted to a narrow supporting structural framework with each distributor flush or recessed at the top surface as desired. The use of hexagonal cups and diverging distributors will be found highly desirable to fit adjacent units close together and eliminate possible areas of stagnant solids. Further, a multiplicity of distributors as shown can be used with a single windbox fitted to a multiplicity of individual treatment section tubes in a multi-tubular reactor.

The various possible configurations of the mouth of the cup notwithstanding, it is generally unobstructed and defined by an outer lip portion. The lip portion, as shown on the drawings, is in periferally closed relationship with the opening of the cone-shaped distributor defined by its truncated apex.

Where multi-tubular reactors are employed, it has been found that better gas distribution among the tubes is obtained where the bottom of the tubes are located well up stream from the gas conduit in cup 9. It has also been found that with the use of a check-valve in the gas conduit, multi-tubular reactors are more effective because back-flow and loss of catalyst are completely prevented.

In operation, pressurized gas is introduced into gas conduit 11 and directed toward the base of cup 9. The particles to be fluidized are blown from cup 9 upwardly, through distributor cone 1 into the base of reactor 2 wherein they are held in uniform suspension by the continued flow of gas.

We have found that with the improvement of the instant invention, excellent distribution of fluidized bed particles is obtained without interruption or clogging of any orifices, tubes, or screens. Moreover the need for the ultra-clean gas feed streams, which are required for porous plate and fine screen distributors, is eliminated. Under sufficient gas pressure, the catalyst bed is maintained in a fluidized state within the distributor and/or the lower portion of the reactor. We have found that with the T-shaped gas conduit, a more uniform distribution of particles is obtained. Corrosion of the T-shaped tube and cup is minimized because the catalyst is suspended above the cup 9 at normal fluidization gas flows. The catalyst drops back into the cup at low or no gas flow condition. When a fluid bed is started up pressure builds up in the bottom head of the reactor and reaches a maximum just before the bed begins fluidizing. After fluidization, the pressure drops below the maximum.

The maximum pressure is minimized by this invention because catalyst bridging in the distributor area is eliminated.

EXAMPLE

A nickel reactor 13 feet in height and 15 inches in diameter is employed as a fluidized bed reactor. The reactor is enclosed in a 20 inch diameter steel jacket forming an annular heat exchange system with Dowtherm ® A (a diphenyl—diphenyl oxide eutectic) circulating in the steel jacket to heat and/or cool the fluid bed. An 8 inch nickel internal cyclone is located at the top of the reactor and a 20 inch diameter by 18 inch high expanded section is provided at this point. Located in the bottom of the reactor is the distribution system shown at FIG. 1. Also located in the bottom of the reactor 14 inches above the distributor plate is a nickel ring utilized to feed oxygen to the reactant zone. The reactor is filled to a depth of 8 feet with a catalyst material comprising copper chloride-potassium chloride impregnated on Florex (calcined fuller's earth manufactured by the Floridin Corporation), prepared as described in U.S. Pat. No. 3,345,422.

Two gas feed lines are provided for the introduction of oxygen, hydrocarbon chlorides and/or hydrocarbons and a chlorinating agent. One of the feed lines terminates in gas conduit 10 reactor wind box. The second feed line is connected to the ring located up in the bed. Utilizing this apparatus, ethylene dichloride and elemental chlorine are fed to Cup 9 of the reactor and oxygen to the ring in a molar feed ratio of ethylene dichloride to chlorine to oxygen of 1.0 to 0.54 to 1.02. With a bed temperature of 766° F. to 819° F. the linear gas velocity is regulated at 0.53 to 0.58 foot per second. A per-tri composition having a weight ratio of 0.98 is obtained from ethylene dichloride.

We claim:

1. In a method of chlorinating a member of the group consisting of aliphatic hydrocarbons having 1 to 2 carbon atoms, their incompletely chlorinated derivatives and benzene by passing a member of the group to be chlorinated, oxygen and a chlorinating agent selected from the group consisting of chlorine, HCl and mixtures of chlorine and HCl in the vapor phase through a fluidized bed of metal halide catalyst particles, the improvement comprising fluidizing the particles by employing a gas distribution system comprising in combination:
   (a) a generally cup-shaped container having a generally circular unobstructed mouth portion defined by an outer lip portion and a base portion;
   (b) pressurized gas introduction means for the introduction of the gas within the container substantially vertically through a tube directed toward the base portion;
   (c) a generally inverted cone-shaped gas distributor having a truncated apex defining a generally circular opening;
   (d) means for holding the outer lip portion of the container in a periferally closed relationship with the opening defined by the truncated apex of the cone-shaped distributor;

so that when in an operating mode the metal halide catalyst particles are distributed uniformly and suspended generally above the cone-shaped distributor by the pressurized gas.

2. The method improvement of claim 1 wherein the gas introduction means is a generally T-shaped tube-like gas conduit comprising a substantially horizontal cross-tube and a substantially vertical discharge tube, the cross-tube extending across and through the lip portion of the container, the discharge tube being connected to the cross-tube and having an opening directed toward the base portion of the container, whereby gas may be introduced.

3. The method improvement of claim 1 wherein the gas introduction means is a generally L-shaped tube-like gas conduit comprising a substantially horizontal cross-tube and a substantially vertical discharge tube, the cross-tube extending horizontally through one side of the lip portion of the container, the discharge tube being connected to the cross-tube and having an opening directed toward the base portion of the container, whereby gas may be introduced.

4. The method improvement of claim 1 wherein the section of truncation defines a circular opening.

5. The method improvement of claim 1 wherein the section of truncation defines a polygonal opening.

6. The method improvement of claim 1 wherein the section of truncation defines a square opening.

7. In a method of chlorinating a member of the group consisting of aliphatic hydrocarbons having 1 to 2 carbon atoms, their incompletely chlorinated derivatives and benzene by passing a member of the group to be chlorinated, oxygen and a chlorinating agent selected from the group consisting of chlorine, HCl and mixtures of chlorine and HCl in the vapor phase through a fluidized bed of metal halide catalyst particles, the improvement comprising fluidizing the particles by employing a gas distribution system comprising in combination:
   (a) a plurality of generally cup-shaped containers each having generally circular unobstructed mouth portions defined by outer lip portions and base portions;
   (b) pressurized gas introduction means for the introduction of the gas within each container substantially vertically through a tube directed toward the base portion of each container;
   (c) a plurality of generally a cone-shaped gas distributors each having a truncated apex, the section of truncation defining an opening;
   (d) means for holding the outer lip portions of the containers in periferally closed relationship with the opening defined by the truncated apex of each cone-shaped distributor;

so that when in an operating mode the metal halide catalyst particles are distributed uniformly and suspended generally above the cone-shaped distributors by the pressurized gas.

8. The method improvement of claim 7 wherein pressurized gas introduction means includes a single chamber for pressure equalization.

* * * * *